(12) United States Patent
Leifeld

(10) Patent No.: US 6,249,935 B1
(45) Date of Patent: *Jun. 26, 2001

(54) APPARATUS FOR REMOVING FOREIGN MATERIAL FROM A FIBER PROCESSING LINE

(75) Inventor: Ferdinand Leifeld, Kempen (DE)

(73) Assignee: Trützschler GmbH & Co. KG, Mönchengladbach (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,058

(22) Filed: Feb. 19, 1999

(30) Foreign Application Priority Data

Feb. 19, 1998 (DE) .................. 198 06 894
Oct. 14, 1998 (DE) .................. 198 47 237

(51) Int. Cl.⁷ ...................................... D01B 3/00
(52) U.S. Cl. .............. 19/204; 19/65 A; 19/200; 19/205; 209/580; 209/639
(58) Field of Search .................. 19/65 A, 105, 19/106 R, 145.5, 200, 202, 203, 204, 66 R, 65 R, 205; 209/580, 581, 577, 639; 406/3, 10, 11, 19, 69, 70

(56) References Cited

U.S. PATENT DOCUMENTS

| | | |
|---|---|---|
| 2,166,925 | 7/1939 | Mitchell et al. . |
| 2,929,112 | 3/1960 | Massey et al. . |
| 4,839,943 * | 6/1989 | Leifeld .................. 19/80 R |
| 4,858,277 * | 8/1989 | Pinto et al. .............. 19/200 |
| 5,205,019 * | 4/1993 | Schnlichter et al. ........ 19/200 |
| 5,522,119 * | 6/1996 | Leifeld et al. ........... 19/106 R |
| 5,626,237 * | 5/1997 | Hergeth .................. 209/580 |
| 5,692,622 | 12/1997 | Hergeth . |
| 5,761,771 * | 6/1998 | Leifeld .................. 19/200 |
| 5,791,489 * | 8/1998 | Leifeld .................. 209/639 |
| 5,819,373 * | 10/1998 | Schlichter et al. .......... 19/205 |

FOREIGN PATENT DOCUMENTS

| | | |
|---|---|---|
| 1 096 808 | 1/1961 | (DE) . |
| 84 31 649 | 2/1985 | (DE) . |
| 87 13 684 | 3/1989 | (DE) . |
| 43 40 165 | 6/1995 | (DE) . |
| 43 40 173 | 6/1995 | (DE) . |
| 195 16 569 | 11/1996 | (DE) . |
| 195 18 762 | 11/1996 | (DE) . |
| 195 18 783 | 11/1996 | (DE) . |
| 195 18 785 | 11/1996 | (DE) . |
| 195 43 526 | 5/1997 | (DE) . |
| 195 47 819 | 6/1997 | (DE) . |
| 37 03 449 | 7/1998 | (DE) . |
| 0 606 626 | 7/1994 | (EP) . |
| 2 210 907 | 6/1989 | (GB) . |
| 96/35831 | 11/1996 | (WO) . |

\* cited by examiner

*Primary Examiner*—John J. Calvert
*Assistant Examiner*—Gary L. Welch
(74) *Attorney, Agent, or Firm*—Venable; Gabor J. Kelemen

(57) ABSTRACT

A fiber processing machine includes a rotatably supported clothed opening roll; a withdrawing roll adjoining the opening roll and supported for rotation for forwarding the fiber material to the opening roll; an optical sensor system for detecting foreign material carried on the opening roll along with fiber material; an air stream generating device for directing an air blast to the clothing of the opening roll; a control-and-regulating device to which the optical sensor system and the air stream generating device are connected for operating the air stream generating device upon detecting foreign material by the optical sensor system to remove and carry away the foreign material from the clothing of the opening roll by an air stream; and a collecting chamber for receiving the air stream carrying the foreign material.

16 Claims, 7 Drawing Sheets

APPARATUS FOR REMOVING FOREIGN MATERIAL FROM A FIBER PROCESSING LINE

CROSS REFERENCE TO RELATED APPLICATION

This application claims the priority of German Application Nos. 198 06 894.8 filed Feb. 19, 1998 and 198 47 237.4 filed Oct. 14, 1998, which are incorporated herein by reference.

BACKGROUND OF THE INVENTION

This invention relates to an apparatus for removing foreign material from a rapidly rotating fiber opening roll of a fiber processing machine which may form part of a fiber processing line. The clothing of the opening roll is associated with at least one feed roll (also referred to hereafter as withdrawing roll), a cover and an optical sensor system for recognizing foreign material. The optical sensor system is connected with an electric control-and-regulating device which, in turn, is coupled to a device which removes the foreign material and which includes a mechanism for generating an air blast directed to the clothing of the opening roll for dislodging and carrying away the foreign material from the clothing of the opening roll.

German Offenlegungsschrift (application published without examination) No. 195 43 526 discloses an apparatus in which two slowly rotating feed rolls laterally cooperate with the opening roll for advancing the fiber material thereto. Guide plates are provided for maintaining the co-rotating air screen on the opening roll. At the lower end of the opening roll a sensor device is disposed for optically recognizing foreign bodies in the fiber tufts. The sensor device is disposed in a collecting chamber for the separated foreign parts. Between the guide plate and a knife an aperture is provided through which, for a short period of time, an air blast is directed from below in an oblique orientation to that region of the roll surface where the fiber tufts contain the foreign bodies. As a result, the contaminated fiber tufts are blown off the roll surface and are subsequently carried away.

It is a disadvantage of the above-outlined prior art device that it needs substantial space because of the lateral introduction of the fiber tufts from a laterally arranged accumulator, conveyor or the like and also because of the arrangement of the optical sensor device and the blowing direction of the air-blast generating source in the region underneath the opening roll. It is a particular drawback that the air-blast generating device is situated in the waste collecting chamber which may lead to significant operational disturbances, interruptions and down times.

SUMMARY OF THE INVENTION

It is an object of the invention to provide an improved fiber processing machine of the above-outlined type from which the discussed disadvantages are eliminated and which, in particular, is structurally simple and compact.

This object and others to become apparent as the specification progresses, are accomplished by the invention, according to which, briefly stated, the fiber processing machine includes a rotatably supported clothed opening roll; a withdrawing roll adjoining the opening roll and supported for rotation for forwarding the fiber material to the opening roll; an optical sensor system for detecting foreign material carried on the opening roll along with fiber material; an air stream generating device for directing an air blast to the clothing of the opening roll; a control-and-regulating device to which the optical sensor system and the air stream generating device are connected for operating the air stream generating device upon detecting foreign material by the optical sensor system to remove and carry away the foreign material from the clothing of the opening roll by an air stream; and a collecting chamber for receiving the air stream carrying the foreign material.

By virtue of the fact that the air stream is guided into a collecting chamber, the air stream, together with the contaminated fibers (that is, fibers intermingled with the foreign bodies) may be captured and its velocity reduced. Swirling of the air is prevented and, at the same time, the fibers and the foreign bodies are collected. Such a capture occurs in the desired direction and at a suitable location. The provision of such a collecting chamber eliminates a source of danger posed by the powerful air stream.

By providing, according to a further feature of the invention, for the fiber material a substantially vertical feed chute, at the lower end of which a withdrawing roll and therebelow an opening roll are disposed, the fiber material is presented to the clothing of the opening roll by the withdrawing roll from above. The withdrawing roll at the same time serves as a feed roll for the opening roll and is disposed adjacent an upper region of the opening roll. Such an arrangement saves horizontal space in the blow room.

The invention has the following advantageous additional features:

- The collecting chamber is situated adjacent the opening roll.
- The collecting chamber is dimensioned such that the air stream expands therein upon introduction.
- The compressed air stream generates a suction stream.
- The suction stream tears away the fibers with the foreign bodies from the opening roll, and has a velocity of, for example, 10–25 m/sec.
- The compressed air stream is discharged by sectional nozzles.
- The air stream carrying fibers and foreign bodies from the clothing of the opening roll passes through a channel which opens into the collecting chamber and which is provided with a stream-deflecting member.

DESCRIPTION OF THE PREFERRED EMBODIMENTS

Figure 1:
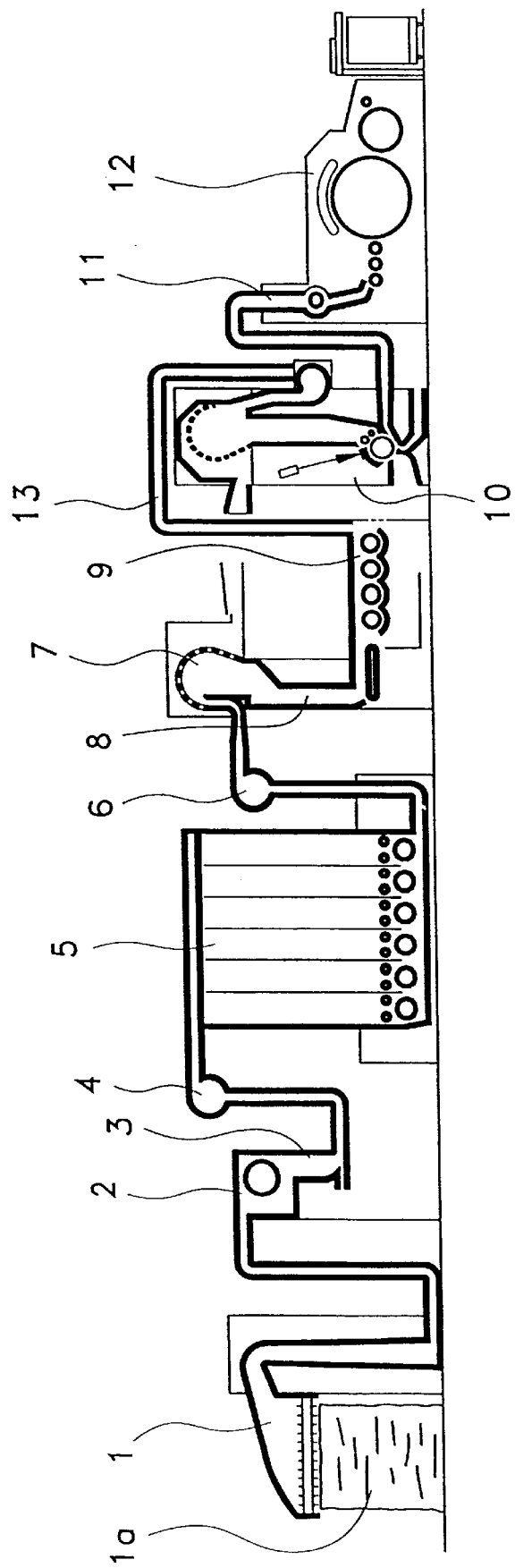
FIG. 1 is a schematic side elevational view of a fiber opening, cleaning and carding line incorporating the invention.

FIG. 1 illustrates a fiber processing line whose first machine is a bale opener 1 which may be a BLENDOMAT BDT model, manufactured by Trützschler GmbH & Co. KG, Monchengladbach, Germany. Between the bale opener 1 and a fiber mixer 5 a high-capacity condenser 2 is arranged which is followed by a feed chute 3 and a fiber transporting fan 4. The mixer 5 is followed by a further fiber transporting fan 6, a fiber separator 7, a feeding device 8 and a multi-roll cleaner 9. The cleaner 9 is followed by the apparatus 10 according to the invention which, in turn, is adjoined in the downstream direction by at least one card feeder 11 and one carding machine 12 which may be, for example, an EXACTACARD DK model manufactured by Trützschler GmbH & Co. KG. Underneath the bale opener 1 a bale series 1a is positioned (only one bale is visible); the bale opener 1 travels over the bale series 1a in a direction perpendicular to the plane of drawing FIG. 1 while it removes fiber material from the top of the fiber bales. The above-described machines are serially connected by pneumatic conduits 13. It is noted that the directions "upstream" and "downstream" are related to the direction in which the fiber material travels through the fiber processing line.

Figure 2:
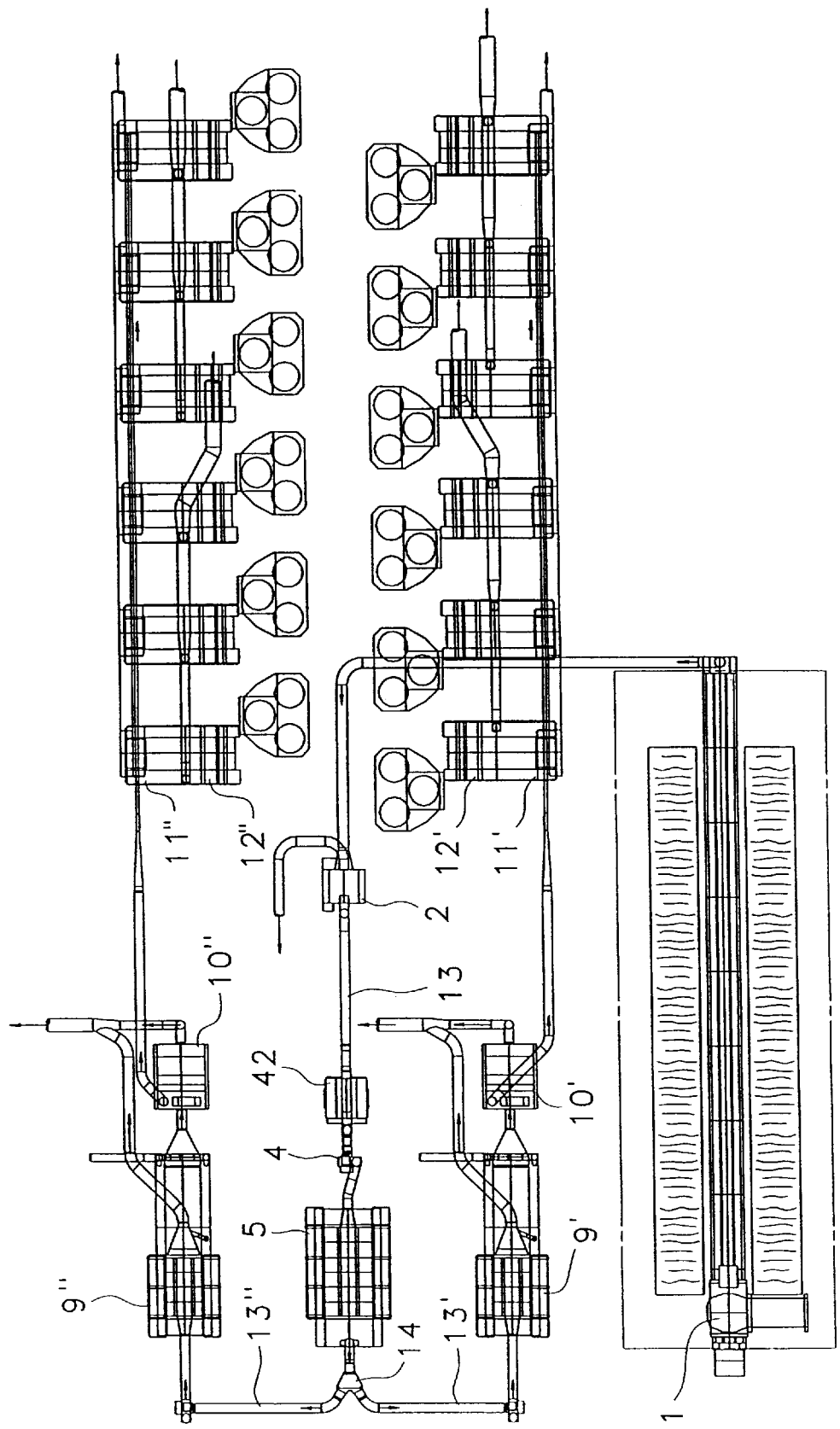
FIG. 2 is a schematic top plan view of a fiber processing line similar to FIG. 1 incorporating two apparatuses according to the invention.

Turning to FIG. 2, in the cotton cleaning line shown therein the mixer 5 is followed by a branch-off device 14 whose conduits 13', 13" lead to respective sawtooth cleaners 9', 9", each of which may be a CLEANOMAT CVT model, manufactured by Trützschler GmbH & Co. KG. Downstream of each sawtooth cleaner 9', 9" respective apparatuses 10' and 10" structured according to the invention are connected which, in turn, are followed by card feeders 11', 11" and associated carding machines 12', 12". Upstream of the mixer 5 a dual-roll cleaner 42 is positioned which may be an AXI-FLO model manufactured by Trützschler GmbH & Co. KG.

Figure 3:
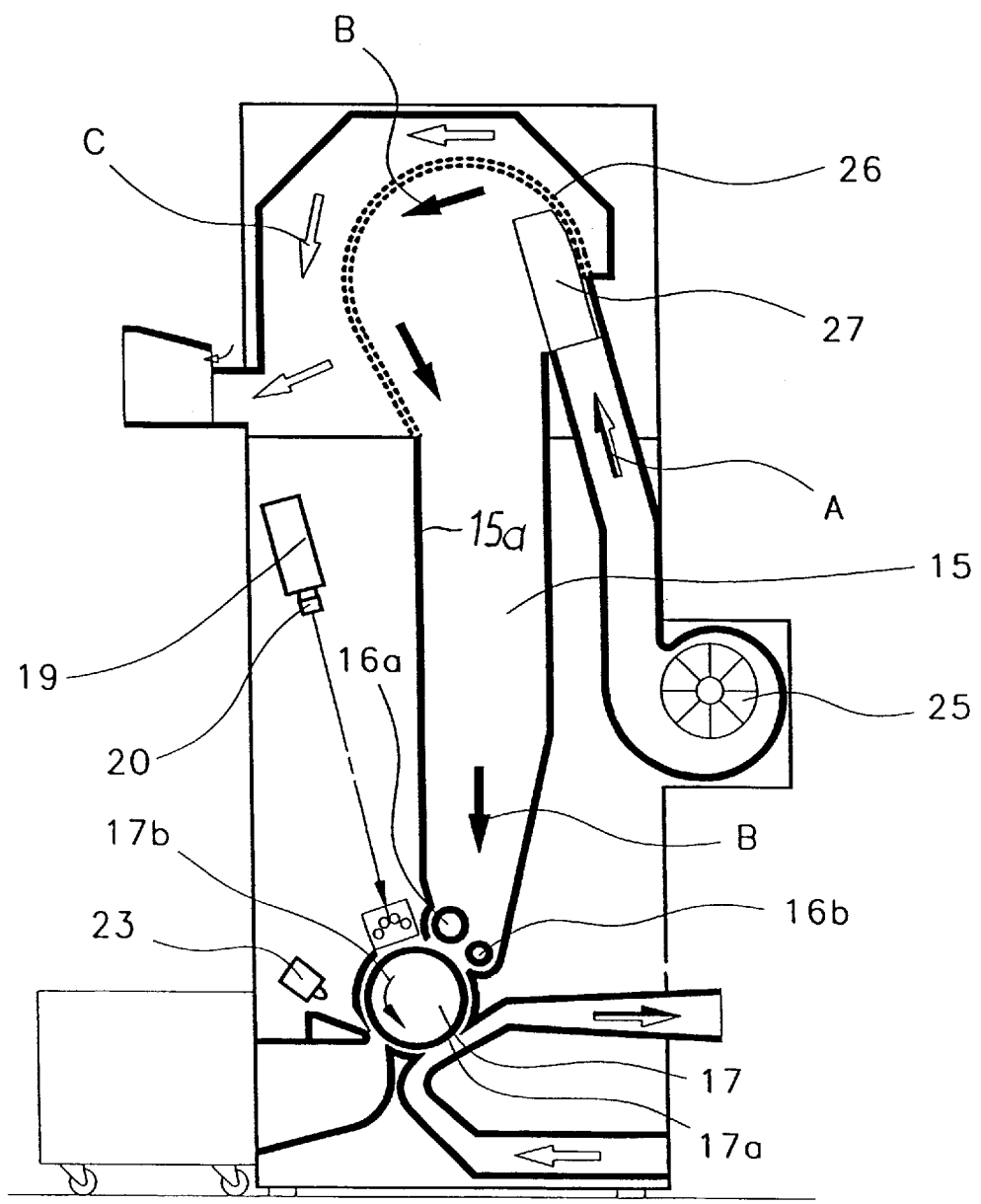
FIG. 3 is a schematic sectional side elevational view of a preferred embodiment of the invention including a feed chute and an after-connected opening roll as well as foreign material recognition and removal devices.
Figure 4:
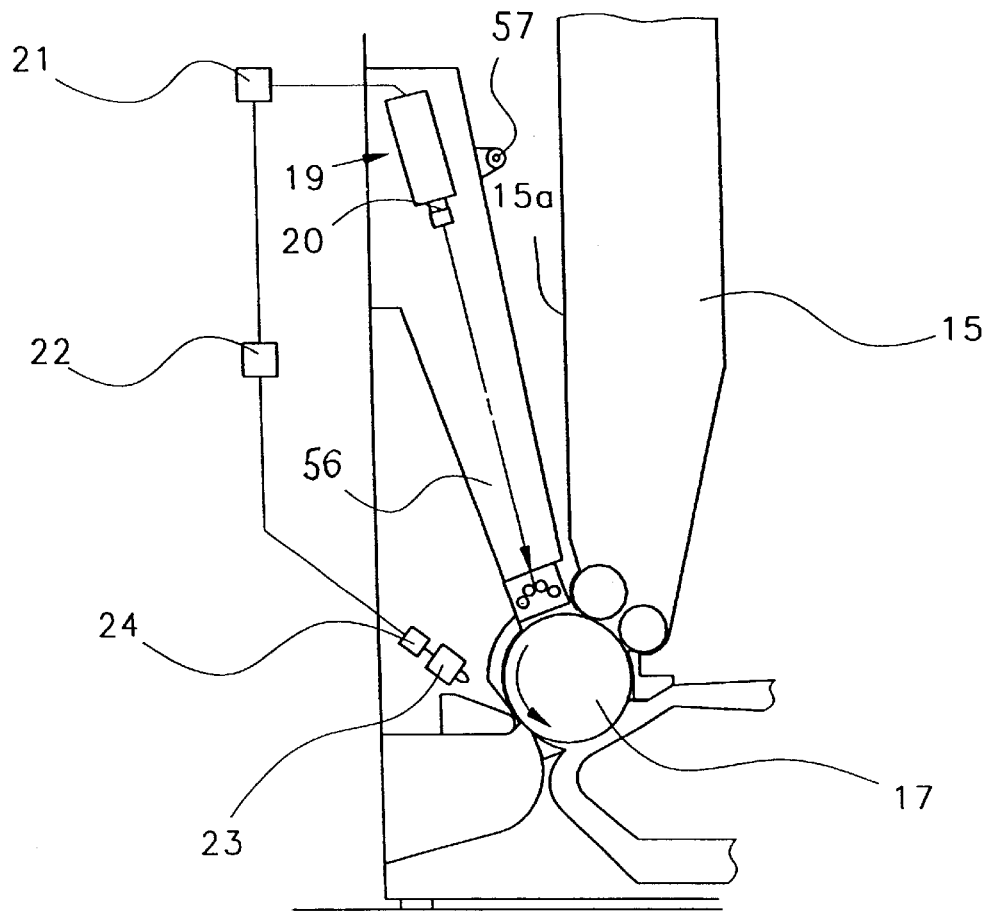
FIG. 4 is a schematic sectional side elevational view of an optical sensor system forming part of the invention and including a camera disposed adjacent a feed chute and oriented toward the opening roll.
Figure 5:
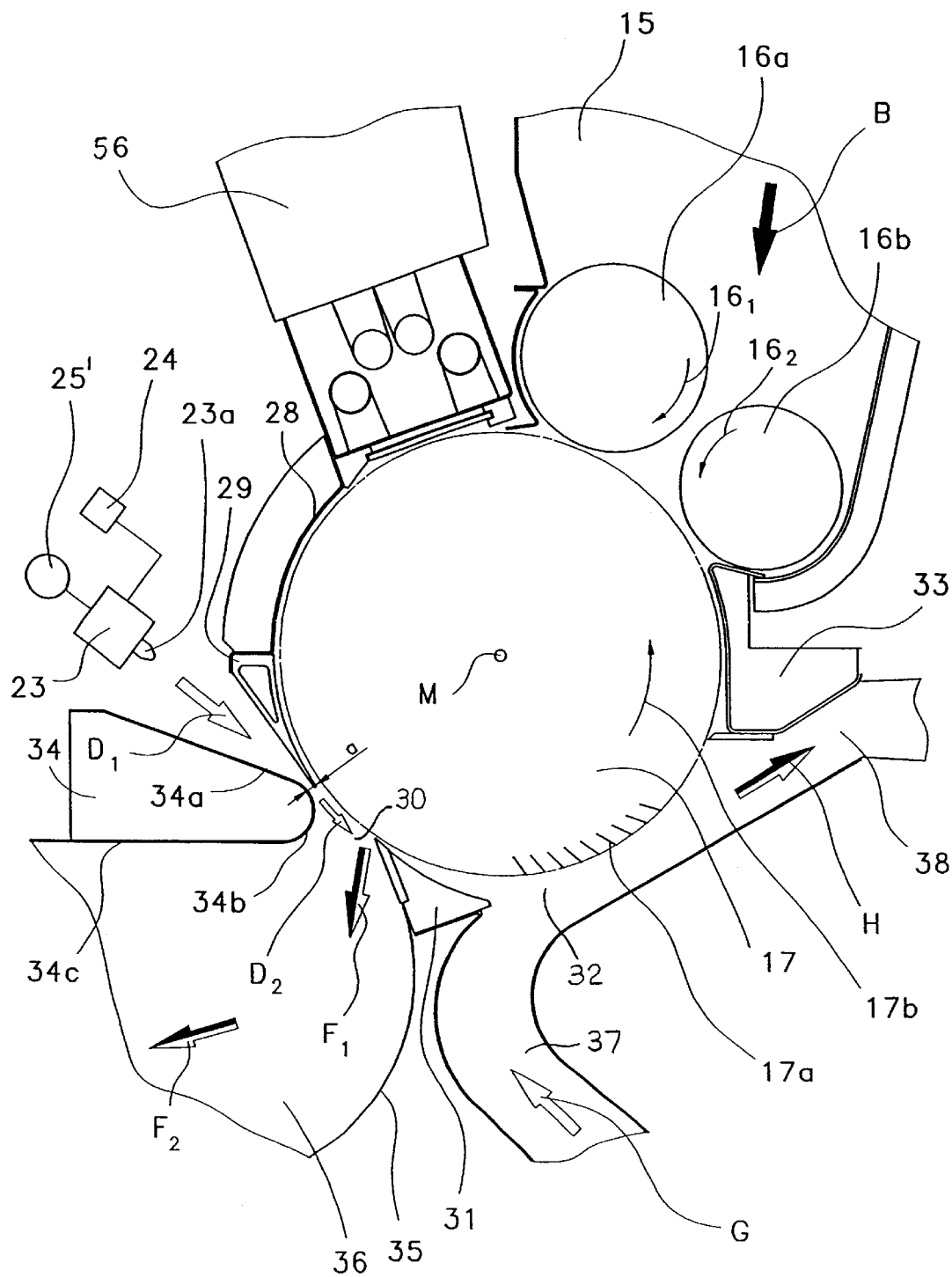
FIG. 5 is a schematic sectional elevational view of a device generating an air blast tangentially to an opening roll and having means for removing the air stream carrying foreign material.

Turning to FIGS. 3, 4 and 5, a substantially vertical tuft feed chute 15 has, at its lower end, two slowly rotating feed rolls (withdrawing rolls) 16a and 16b which introduce fiber material to a rapidly rotating opening roll 17 having a clothing 17a and a direction of rotation 17b. The withdrawing rolls 16a, 16b which rotate in the direction $16_1$ and $16_2$, respectively, are situated in the immediate vicinity of the clothing 17a of the opening roll 17. A camera 20, such as a CCD line camera of an optical sensor system 19 which also includes an electronic evaluating device 21 for recognizing foreign bodies, is directed to the clothing 17a of the opening roll 17. The sensor system 19 recognizes foreign bodies and particles, particularly those which deviate in lightness and color from the fiber material to be processed. The sensor system 19 is connected by means of an electronic control and regulating device 22 with a device 23 for removing the foreign bodies. The device 23 generates a short-duration, powerful air stream (air blast) oriented toward the clothing 17a for dislodging and carrying away foreign bodies with a small quantity of fibers from the clothing 17a.

A fiber transporting fan 25 pneumatically introduces fiber material into an upper inlet opening of the feed chute 15. A stationary, air-pervious surface (screen) 26 arranged at the top of the feed chute 15 separates the fiber material from the air stream which thus exits the feed chute 15, while the fiber material proceeds toward the withdrawing rolls 16a, 16b. Further in the upper part of the feed chute 15 an air stream guiding device 27 having movable elements is disposed for effecting a back-and-forth agitation of the fiber material at the inner face of the screen 26 as the air stream separates therefrom and passes through the screen 26. Eventually, the fiber material, substantially by gravity, drops down into the feed chute 15. The rolls 16a, 16b have a dual function: they serve as withdrawing rolls for the fiber material by pulling it downwardly in the feed chute 15 and also serve as feed rolls for presenting the fiber material to the opening roll 17.

The solid arrows in FIGS. 3, 5, 6, 7 and 7a illustrate fiber material flow, while the empty arrows indicate air streams without fibers and the half solid, half empty arrows designate fiber-laden air streams.

The camera 20 is situated, as shown in FIGS. 3 and 4, obliquely above the opening roll 17 in the vicinity of the outer wall 15a of the feed chute 17, whereby a compact, space-saving construction is obtained. The camera 20 is oriented towards the clothing 17a of the opening roll 17 and is capable of recognizing colored foreign material such as red fibers in the fiber flow. The range of the camera 20 includes the full axial length of the opening roll 17 which may be, for example, 1 m. As viewed in the direction of rotation 17b of the opening roll 17, downstream of the optical sensor system 19 the device 23 for generating a pneumatic stream is arranged which has a nozzle 23a oriented in the direction of the clothing 17a of the opening roll 17 in such a manner that a short-duration, powerful air stream flows to the clothing 17a, approximately tangentially thereto. The sensor system 19 is coupled via the evaluating device 21 and the electronic control-and-regulating device 22 with the air-blast generating device 23 which includes a valve control device 24. When the camera 20, based on comparison values or desired values, detects foreign material in the fiber mass situated on the clothing 17a, the valve control device 24 sends a command to the device 23 to emit a short, high-speed air blast toward the clothing 17a to remove the foreign material from the fiber layer on the clothing 17a with a small number of fibers.

Figure 4A:
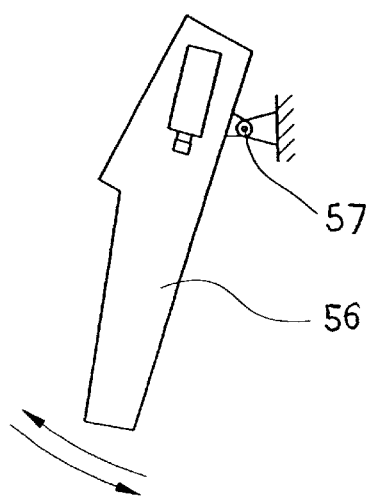
FIG. 4a is a schematic sectional side elevational view of the camera of FIG. 4, illustrated in a position pivoted away from the opening roll.

The sensor system 19 is accommodated in a housing 56 which, as shown in FIG. 4a, may be pivoted inwardly and outwardly about a stationary rotary support 57.

Turning to FIG. 5, the two withdrawing rolls 16a and 16b are arranged obliquely above the rotary axis M of the opening roll 17, adjacent the clothing 17a thereof. As viewed in the rotary direction 17b, downstream of the withdrawing rolls 16a, 16b a cover 28, a cover element 29, an opening 30, a cover element 31, an opening 32 and a cover element 33 are arranged in a circumferential series about the opening roll 17. The device 23 is coupled to a pressurized air source 25'. The valve control device 24 opens a non-illustrated valve of the separating device 23 for a short period so that a strong air jet $D_1$, with a high speed of, for example, 15–25 m/sec is discharged by the nozzle 23a of the separating device 23. Expediently, a non-illustrated nozzle bank with several linearly arranged nozzles 23a is provided which extends over the width (axial length) of the opening roll 17. The cover 29 and a guide face 34a of an oppositely situated guide element 34 are arranged conically with respect to one another and have, at their narrowest clearance, a distance a from one another through which the air stream $D_2$ passes in such a manner that it flows at a small distance from the clothing 17a. As a result, a suction stream $F_1$ is generated (based on the principle of a water jet pump) which, for a short period of time, locally tears away a small quantity of fibers together with the foreign material from the fiber layer carried on the clothing 17a. The guide element 34 has a rounded nose 34b and a further guide face 34c which, together with an oppositely disposed deflecting element 35, forms a channel 36 for guiding the air stream $F_2$ away from the opening roll 17. An air stream G flows in the direction of the opening roll 17 through a channel 37 toward the opening 32 for dislodging the fiber layer from the clothing 17a and flows through a channel 38 as a fiber-laden stream H.

Figure 6:
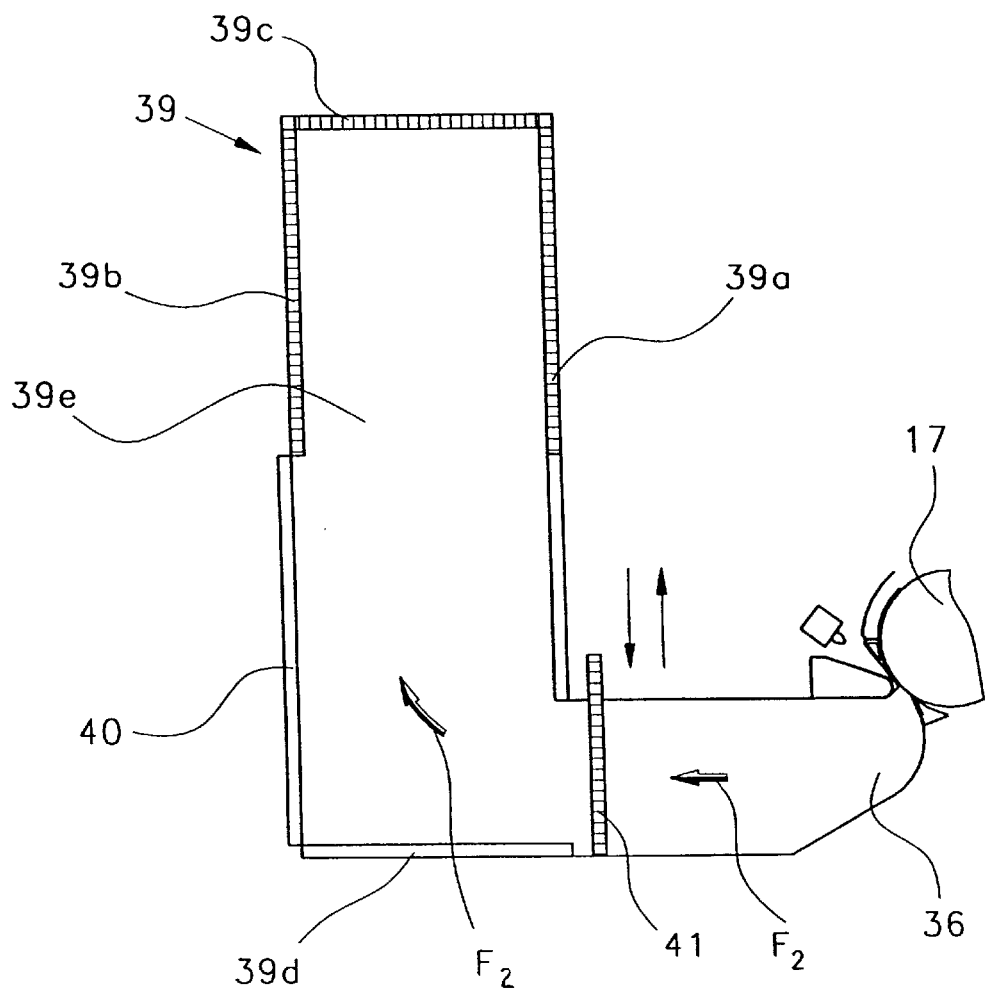
FIG. 6 is a schematic side elevational view of an air expansion and waste collecting chamber forming part of the invention.
Figure 6A:
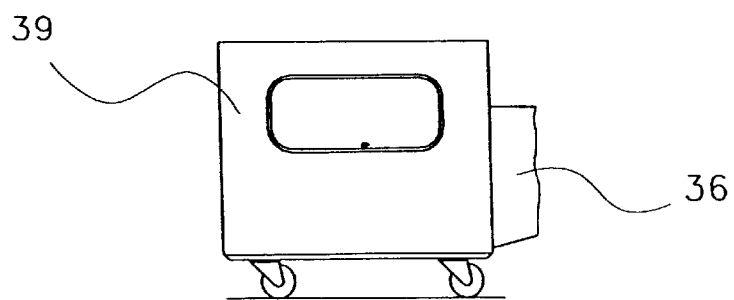
FIG. 6a is a schematic side elevational view of an air expansion and waste collecting chamber designed as a removable carriage.

Turning to FIG. 6, laterally of the feed chute 15 and the optical sensor system 19 a receptacle 39 is disposed, having a bottom 39d and a side wall 39a which is provided with an opening connected to the channel 36. The fiber-laden air stream $F_2$ enters the inner chamber 39e of the receptacle 39. The volume of the chamber 39e is designed such that the air stream $F_2$ expands and its velocity significantly drops. The chamber 39e at the same time serves as a collecting space for the separated fiber material containing the foreign bodies. The side walls 39a, 39b and the top wall 39c of the receptacle 39 are formed as air-pervious screens to allow the air stream to be separated from the foreign material and to thus exit the receptacle 39. In the plane of the side wall 39b an access door 40 is provided through which the waste collected in the chamber 39e may be periodically removed. Between the end of the channel 36 and the opening in the wall 39a an air-pervious slidable gate 41 is provided which is displaceable in the direction of the two arrows when the access door 40 is opened or, respectively, closed. Preferably, the receptacle 39 is of upright design, whereby horizontal space may be saved. As shown in FIG. 6a, the receptacle 39 is part of a wheeled carriage which may be connected to or disconnected and moved away from the channel 36. The further wall faces of the receptacle 39 oriented perpendicularly to the walls 39a, 39b are not illustrated.

Figure 7:
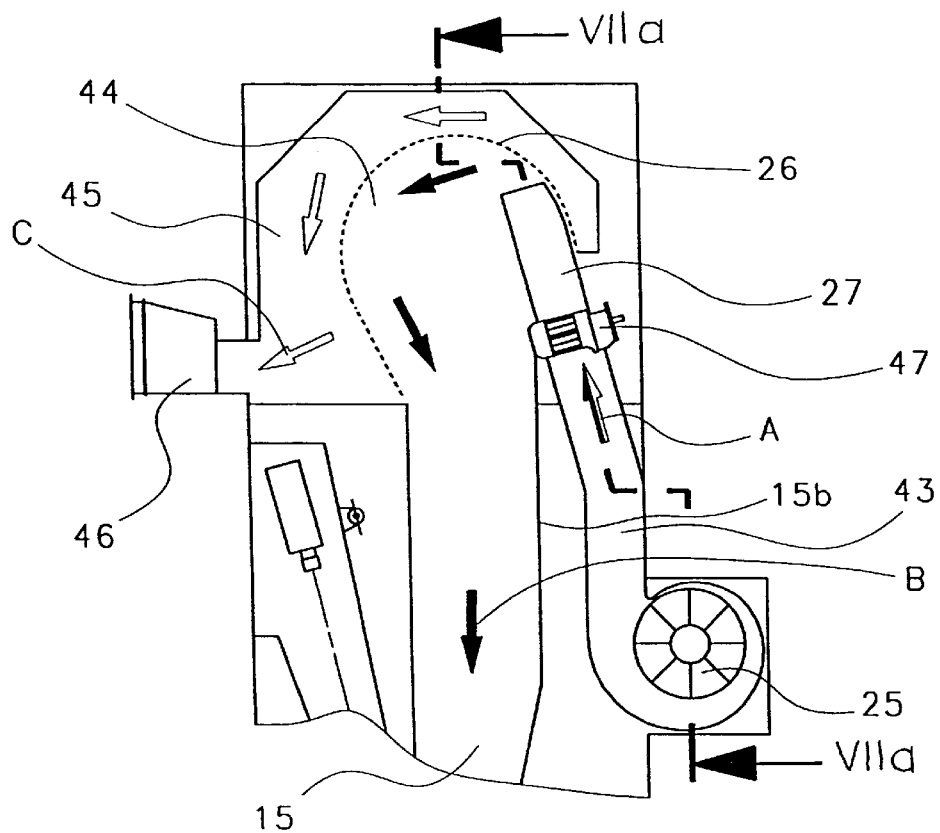
FIG. 7 is a schematic sectional side elevational view of a device for separating fiber material from the air stream.

As shown in FIG. 7, the fiber material transporting fan 25 is arranged laterally of the wall 15b of the feed chute 15. The fan 25 blows the fiber-laden air stream A (discharged, for example, by an upstream-arranged machine of the fiber processing line) through the conduit 43 into a chamber 44 in which the stationary, semi-cylindrical, air-pervious screen 26 is provided for separating the fiber material B from the air stream. The air stream C thus stripped of the fiber material (but still containing dust) passes through the screen 26 into the chamber 45 and exits through an outlet 46. The conduit 43 is adjoined by an air guiding device 27 having movable elements, whereby a reversible, back-and-forth guidance of the material in the air stream may be effected, and the fiber material B, after impinging on the air-pervious surface 26, drops downwardly essentially by gravity and is introduced into the feed chute 15. The outlet end of the conveying conduit 43 merges into the chamber 44 approximately tangentially to the screen 26. During operation, the stream A, after impinging on the screen 26, sweeps therealong and thus has a cleaning effect thereon. The perforations (meshes) of the screen 26 have a size which is sufficient to allow passage of the dust-laden air stream C and small impurities on the fiber tufts but prevents passage of the fiber tufts B.

Figure 7A:
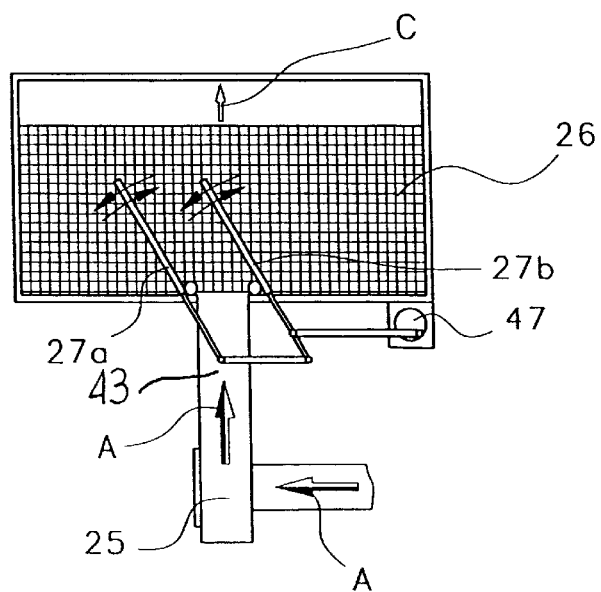
FIG. 7a is a sectional view taken along line VIIa-VIIa of FIG. 7.

Turning to FIG. 7a, the earlier-noted back-and-forth guidance of the fiber-laden air stream A is effected by a pair of oscillating guide plates 27a, 27b whose surfaces are essentially parallel to one another and are driven, for example, by a motor 47. The outlet opening of the conduit 43 is situated in the space between the two guide plates 27a, 27b.

The invention also encompasses an embodiment in which the feed chute 15 serves as a fiber accumulator in a cleaning line such as shown in FIG. 1. Expediently, the feed chute 15 has a filling height regulating device including, for example, an optical barrier or the like, and further, the rpm of one or both withdrawing rolls 16a, 16b may be regulated. Preferably an electronic control-and-regulating device such as a microcomputer 22 is provided to which there are connected the setting member for the rpm of at least one of the feed rolls 16a, 16b and at least one measuring member sensing the fill level in the after-connected card feeder chutes 11 for the cards 12. Expediently, at the card feeders 11 electronic pressure switches are used as measuring members, and to the control-and-regulating device 22 an element is connected for determining a basic operating rpm as a function of the sum of all productions of the cards 12.

The invention also encompasses an embodiment in which the optical sensor system 19 is installed in a multi-roll cleaner 9 (FIG. 1) and is associated with a first opening roll, whereas the device 23 for generating the air blast is associated with the last opening roll, as viewed in the direction of fiber travel through the cleaner.

It will be understood that the above description of the present invention is susceptible to various modifications, changes and adaptations, and the same are intended to be comprehended within the meaning and range of equivalents of the appended claims.

What is claimed is:

1. A fiber processing machine comprising
   (a) a rotatably supported opening roll having a clothing arranged circumferentially thereon;
   (b) a withdrawing roll adjoining said opening roll and being supported for rotation for forwarding the fiber material to said opening roll;
   (c) an optical sensor system to detect foreign material carried on said opening roll along with said fiber material;
   (d) an air stream generating device to direct an air blast to said clothing;
   (e) a control-and-regulating device; said optical sensor system and said air stream generating device being connected to said control-and-regulating device for operating said air stream generating device upon detecting foreign material by said optical sensor system to remove and carry away the foreign material from said clothing of said opening roll by an air stream; and
   (f) means defining a collecting chamber for receiving said air stream carrying the foreign material.

2. The fiber processing machine as defined in claim 1, wherein said means defining said collecting chamber comprises wall portions constituted by screens for allowing the air stream to exit the collecting chamber.

3. The fiber processing machine as defined in claim 1, wherein said means defining said collecting chamber comprises a wheeled carriage.

4. The fiber processing machine as defined in claim 1, wherein said means defining said collecting chamber comprises an access door for removing waste material accumulated in said collecting chamber.

5. The fiber processing machine as defined in claim 1, wherein said collecting chamber has an upright-oriented design.

6. The fiber processing machine as defined in claim 1, wherein said collecting chamber extends generally parallel to said optical sensor system and is disposed laterally thereof.

7. The fiber processing machine as defined in claim 1, wherein said means defining said collecting chamber has top, bottom and side walls.

8. The fiber processing machine as defined in claim 1, further comprising
   (g) a generally vertically oriented feed chute having an upper portion and a lower portion; said withdrawing roll and said opening roll are positioned in said lower portion of said feed chute; and
   (h) means for introducing fiber material into said upper portion of said feed chute.

9. The fiber processing machine as defined in claim 8, wherein said collecting chamber is disposed laterally of said feed chute.

10. The fiber processing machine as defined in claim 9, wherein said collecting chamber is disposed adjacent said opening roll.

11. The fiber processing machine as defined in claim 1, further comprising a channel having an inlet adjacent said opening roll and an outlet merging into said collecting chamber; the air stream being guided into said collecting chamber by said channel.

12. The fiber processing machine as defined in claim 11, further comprising a deflecting element situated within said channel adjacent said opening roll for deflecting said air stream.

13. The fiber processing machine as defined in claim 12, wherein said deflecting element forms part of said channel.

14. The fiber processing machine as defined in claim 11, further comprising an openable and closable gate positioned in said channel.

15. The fiber processing machine as defined in claim 14, wherein said gate element comprises an air-pervious screen.

16. The fiber processing machine as defined in claim 1, wherein said means defining a collecting chamber includes means for expanding the air stream upon entering said collecting chamber.

\* \* \* \* \*